United States Patent [19]

Magerlein

[11] 4,065,629
[45] Dec. 27, 1977

[54] 17-PHENYL-18,19,20-TRINOR-CIS-4,5-DIDEHYDRO-PGA$_1$ COMPOUNDS

[75] Inventor: Barney J. Magerlein, Portage, Mich.

[73] Assignee: The Upjohn Company, Kalamazoo, Mich.

[21] Appl. No.: 741,244

[22] Filed: Nov. 12, 1976

Related U.S. Application Data

[62] Division of Ser. No. 580,747, May 27, 1975, Pat. No. 4,032,561.

[51] Int. Cl.$^2$ ............................................. C07C 69/76
[52] U.S. Cl. ................................. 560/5 B; 260/520 B
[58] Field of Search ...................... 260/473 A, 520 B

[56] References Cited

FOREIGN PATENT DOCUMENTS

| 7,306,461 | 11/1973 | Netherlands | 260/473 A |
| 7,301,094 | 7/1973 | Netherlands | 260/473 A |
| 7,501,560 | 8/1975 | Netherlands | 260/473 A |

*Primary Examiner*—Paul J. Killos
*Attorney, Agent, or Firm*—Robert A. Armitage

[57] ABSTRACT

The disclosure includes novel compounds which differ from the known prostaglandins PGF$_{2\alpha}$, PGF$_{2\beta}$, PGE$_2$, PGA$_2$, and PGB$_2$ in that the carbon-carbon double bond in the carboxyl-terminated chain of the novel compounds is in the 4,5-position rather than in the 5,6-position, and in that there is a phenyl or substituted phenyl group in the other chain of the novel compounds. These novel compounds are useful for a variety of pharmacological purposes, including abortion, labor induction, and reduction of gastric secretion.

7 Claims, No Drawings

17-PHENYL-18,19,20-TRINOR-CIS-4,5-DIDEHYDRO-PGA₁ COMPOUNDS

The present application is a divisional application of Ser. No. 580,747, filed May 27, 1975, now issued as U.S. Pat. No. 4,032,561, on June 28, 1977.

The present invention relates to prostaglandin analogs for which the essential material constituting a disclosure therefor is incorporated by reference here from U.S. Pat. No. 4,032,561, issued June 28, 1977.

I claim:

1. An optically active compound of the formula:

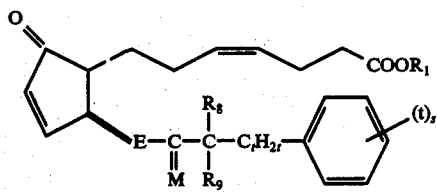

or a racemic form of that compound and the enantiomer thereof, wherein $R_1$ is hydrogen or alkyl of one to 12 carbon atoms, inclusive, cycloalkyl of 3 to 10 carbon atoms, inclusive, aralkyl of 7 to 12 carbon atoms, inclusive, phenyl, or phenyl substituted with one, 2, or 3 chloro or alkyl of one to 4 carbon atoms, inclusive;

wherein M is

or

wherein $R_2$ is hydrogen, methyl, or ethyl;
wherein E is trans—CH=CH— or —CH₂CH₂—;
wherein $R_8$ is hydrogen and $R_9$ is hydrogen, methyl, or fluoro, or wheren $R_8$ and $R_9$ are both methyl or both fluoro, with the proviso that neither of $R_8$ and $R_9$ is methyl when $R_2$ is methyl or ethyl;
wherein $C_tH_{2t}$ represents a valence bond or alkylene of one to 9 carbon atoms, inclusive, with one to 6 carbon atoms, inclusive, between —CR₈R₉— and the ring; and
wherein T is alkyl of one to 4 carbon atoms, inclusive, fluoro, chloro, trifluoromethyl, or —OR₃, wherein $R_3$ is alkyl of one to 4 carbon atoms, inclusive and wherein s is zero, one, 2, or 3 with the proviso that not more than 2 T's are other than alkyl; including alkanoates of 2 to 8 carbon atoms, inclusive, and pharmacologically acceptable salts thereof when $R_1$ is hydrogen.

2. An optically active compound according to claim 1, wherein E is trans—CH=CH—, $R_1$ is hydrogen, methyl, or ethyl, M is

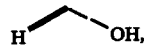

s is zero or one, T when present is chloro, fluoro, or trifluoromethyl, $R_8$ and $R_9$ are methyl, or $R_8$ is hydrogen and $R_9$ is fluoro, and $C_tH_{2t}$ is —CH₂— or —CH₂CH₂—, and pharmacologically acceptable salts thereof when $R_1$ is hydrogen.

3. An optically active compound according to claim 1, wherein E is trans—CH=CH—, $R_1$ is hydrogen, methyl, or ethyl, M is

wherein $R_2$ is hydrogen or methyl, s is zero or one, T when present is chloro, fluoro, or trifluoromethyl, $R_8$ and $R_9$ are hydrogen, and $C_tH_{2t}$ is —CH₂— or —CH₂CH₂—, and pharmacologically acceptable salts thereof when $R_1$ is hydrogen.

4. cis-4,5-Didehydro-17-phenyl-18,19,20-trinor-PGA₁, a compound according to claim 3, wherein $R_1$, $R_2$, $R_8$, and $R_9$ are hydrogen, s is zero, and $C_tH_{2t}$ is —CH₂—.

5. cis-4,5-Didehydro-17-phenyl-18,19,20-trinor-PGA₁, methyl ester, a compound according to claim 3, wherein $R_1$ is methyl, $R_2$, $R_8$, and $R_9$ are hydrogen, s is zero, and $C_tH_{2t}$ is —CH₂—.

6. cis-4,5-Didehydro-15-methyl-17-phenyl-18,19,20-trinor-PGA₁, a compound according to claim 3, wherein $R_1$, $R_8$, and $R_9$ are hydrogen, $R_2$ is methyl, s is zero, and $C_tH_{2t}$ is —CH₂—.

7. cis-4,5-Didehydro-15-methyl-17-phenyl-18,19,20-trinor-PGA₁, methyl ester, a compound according to claim 3, wherein $R_1$ and $R_2$ are methyl, $R_8$ and $R_9$ are hydrogen, s is zero, and $C_tH_{2t}$ is —CH₂—.

* * * * *

UNITED STATES PATENT OFFICE
CERTIFICATE OF CORRECTION

Patent No. 4,065,629                Dated December 27, 1977

Inventor(s) B. J. Magerlein

It is certified that error appears in the above-identified patent and that said Letters Patent are hereby corrected as shown below:

Column 1, line 20, that portion of the structural formula reading  should read 

Signed and Sealed this

Twentieth Day of June 1978

[SEAL]

Attest:

RUTH C. MASON
Attesting Officer

DONALD W. BANNER
Commissioner of Patents and Trademarks